United States Patent

Roelant

[11] Patent Number: 5,998,128
[45] Date of Patent: *Dec. 7, 1999

[54] USE OF PORPHYRINS IN INSTRUMENTAL DETECTION METHODS

[75] Inventor: Chris Roelant, Leuven, Belgium

[73] Assignee: Packard Instrument B.V., Groningen, Netherlands

[*] Notice: This patent is subject to a terminal disclaimer.

[21] Appl. No.: 08/876,093

[22] Filed: Jun. 13, 1997

[30] Foreign Application Priority Data

Jun. 14, 1996 [EP] European Pat. Off. ............. 96201674

[51] Int. Cl.$^6$ .............................. C12Q 1/00; C12Q 1/02
[52] U.S. Cl. ................. 435/4; 435/5; 435/7.21; 435/7.32; 435/7.33
[58] Field of Search ..................... 436/544, 545, 436/546, 172, 805; 435/40.5, 4, 5, 7.21, 7.33, 7.32

[56] References Cited

U.S. PATENT DOCUMENTS

| | | |
|---|---|---|
| 3,754,868 | 8/1973 | Witz et al. . |
| 4,176,007 | 11/1979 | Jeffers et al. . |
| 4,234,681 | 11/1980 | DeLuca-McElroy . |
| 4,375,972 | 3/1983 | Forgione et al. . |
| 4,577,636 | 3/1986 | Spears . |
| 4,672,039 | 6/1987 | Lundblom . |
| 5,108,893 | 4/1992 | Baret . |

FOREIGN PATENT DOCUMENTS

| | | |
|---|---|---|
| 0 070 685 A2 | 1/1983 | European Pat. Off. . |
| 0 480 361 A2 | 4/1992 | European Pat. Off. . |
| 62-135769 | 6/1987 | Japan . |
| 3-047093 | 2/1991 | Japan . |
| 2 063 469 | 6/1981 | United Kingdom . |
| WO 93/12809 | 7/1993 | WIPO . |

OTHER PUBLICATIONS

Yves, Adam, et al., "Luminol And Isoluminol Chemiluminescence Reaction Catalyzed By Synthetic Water–Soluble Metalloporphyrins," *New Journal of Chemistry*, vol. 16, No. 4, pp. 525–528, Apr. 1992.

Ewetz, L., et al., "Factors Affecting The Specificity Of The Luminol Reaction with Hematin Compounds," *Analytical Biochemistry*, vol. 71, pp. 564–570, Apr. 1976.

Olsson, T., et al., "Catalytic Action And Destruction Of Protohematin During Peroxide Dependent Luminol Chemiluminescence," *Photochemistry and Photobiology*, vol. 38, No. 2, pp. 223–229, Aug. 1983.

*Primary Examiner*—Mary E. Ceperley
*Attorney, Agent, or Firm*—Arnold White & Durkee

[57] ABSTRACT

The present invention relates to a process for quantifying entities, comprising the steps of (a) mixing an effective detection amount of a (proto-) porphyrin represented by formula (I)

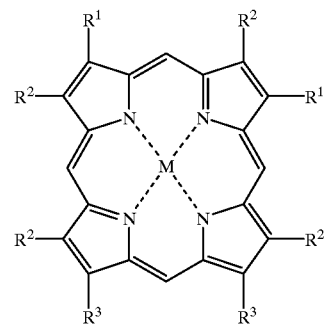

wherein
$R^1$ independently represents a radical selected from the group consisting of —CH(OH)—CH$_3$, —CH=CH$_2$, —CH$_2$—CH$_3$, —H, —COCH$_3$, —CHO, —CH(OH)—CH$_2$OH, and —CH=CHO$_2$H;
$R^2$ independently is selected from C$_{1-3}$ alkyl, and preferably is methyl,
$R^3$ independently represents an aryl or aralkyl group, and preferably is phenyl; and
M is a metal selected from Fe, Co, Ga, Sn, Zn, Cr, Mg, Ni, Ge, and Cu,
with a sample suspected to contain entities to be detected;

(b) collecting the (proto)porphyrin containing complexes formed; and (c) detecting and quantifying the collected complexes.

Further, the invention relates to a chemiluminescent composition comprising a compound defined in formula I.

11 Claims, 8 Drawing Sheets

UNILITE VIRUS LABEL
DSN pJD214MDR1 flux/mm²/10s

| Sample | Value |
|---|---|
| DSN | ~20 |
| DSN+HT | ~380 |
| pJD214 | ~40 |
| pJD214+HT | ~780 |

Figure 7

USE OF PORPHYRINS IN INSTRUMENTAL DETECTION METHODS

The present invention relates to the field of instrumental detection methods, and in particular to processes for labelling, detecting and quantifying chemical, biological and/or physical entities. These entities can for instance be molecules, particles, beads, microorganisms or cells. The present invention additionally relates to light output enhancement of enzymatic and non-enzymatic triggered luminol-type dependent chemiluminescent compositions.

As is generally known, chemical, biological and/or physical entities can be detected and quantified directly and indirectly. Direct analysis is, e.g., carried out by microscopic, nephelometric or electronic enumeration, while indirect analysis makes use of, e.g., chromogenic or fluorogenic dyes, incorporation of radioactive precursors or of metabolic activity of microorganisms and cells. These known techniques generally require labelling of the entities to be detected. In labelling techniques, bridging molecules or metabolic processing is often required.

The techniques known from the prior art as a whole, are labor intensive and/or require long incubation times.

In accordance with the present invention, it has now been found that a particular group of compounds can be used as a rather universal label, which compounds can bind or can be attached very strongly with or to molecules, particles, beads, microorganisms and cells, in general to entities capable to hydrophobic interaction, without requiring any bridging molecules. The binding or attachment is very strong and often irreversible.

After binding or attachment, the complexes formed can be detected either chemiluminometrically, fluorimetrically or radiometrically in an amount which is proportional to the number of labelled entities.

The particular group of compounds which can bind with or be attached to entities to be detected can be represented by Formula (I):

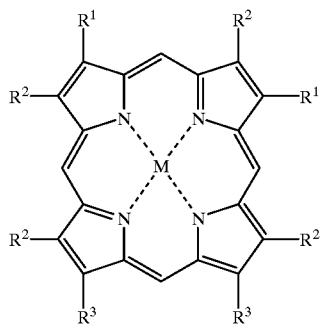

wherein $R^1$ independently represents a radical selected from the group consisting of —CH(OH)—CH$_3$, —CH=CH$_2$, —CH$_2$—CH$_3$, —H, —COCH$_3$, —CHO, —CH(OH)—CH$_2$OH, and —CH=CHO$_2$H;

$R^2$ independently is selected from C$_{1-3}$ alkyl, and preferably is methyl, $R^3$ independently represents an aryl or aralkyl group, and preferably is phenyl; and M is a metal selected from Fe, Co, Ga, Sn, Zn, Cr, Mg, Ni, Ge, and Cu. These compounds are also referred to as porphyrins and protoporphyrins in the present description.

The present invention relates in a first aspect to a process for quantifying entities, comprising the steps of (a) mixing an effective detection amount of a (proto-)porphyrin of formula (I) with a sample suspected to contain entities to be detected;

(b) collecting the (proto)porphyrin containing complexes formed; and (c) detecting and quantifying the collected complexes.

The entity to be detected can be any molecule, particle, bead, microorganism, cell, micel and so on, which at least has a hydrophobic part or at least a part capable to hydrophobic interaction. Non-limiting examples of particles and beads include particles or beads of nylon, polystyrene, polypropene, latex or glass. These particles or beads may carry ligands, haptens or bridging molecules such as biotin, biotin-N-hydroxy-succinimide or binding proteins including avidin, streptavidin and antibodies. Non-limiting examples of microorganisms include gram-positive and gram-negative bacteria, mycoplasma, and viruses. Non-limiting examples of cells include prokaryotic as well as eukaryotic cells, mammalian cells inclusive. The compounds of formula I more or less act as a suction cup on these entities.

The collection of step (b) can be carried out in any known way and in fact is dependent on the entity to be detected. Examples of suitable collecting methods are adhesion, magnetic separation, centrifugation, filtration, and membrane separation.

In step (c) the detection and quantification can for instance be carried out using radiometric techniques. Radiation emission of isotope-labelled compounds of formula I can be detected and is proportional to the number of entities labelled. In this embodiment, the compounds defined by formula I can contain isotopically marked or labelled—e.g. by a suitable substituent—with carbon-14, chlorine-36, cobalt-(57,58,60), gadolinium-153, iron-(55,59), nickel-63, tritium, iodine-125, tin-113 or zino-65; compounds of formula I tritiated or labelled with iodine-125 being preferred. Radiometric detection is used suitably in a system that contains (traces of) porphyrin-like structures, such as traces of blood (haemoglobulin), or chlorophyll-containing substances, which systems may interfere when using other detection methods.

In another embodiment, SPA (scintillation proximity assay) beads are used for the detection and quantification, which beads can be immobilized and can be in suspension. This detection and quantification method comprises the steps of mixing an effective detection amount of isotope labelled compound of formula I with an aqueous suspension in which SPA beads need to be detected and quantified; and measuring the increase in radiation emission, which is proportional to the number of SPA beads.

In yet another embodiment, the detection can be effected by fluorimetry. In this embodiment, the fluorescence signal emitted after light excitation of the compounds having formula I is detected, which light signal is proportional to the number of labelled entities.

The detection step of step (c) of the process of the invention, however, preferably involves a chemiluminometric analysis. In such an analysis, the (proto)porphyrin labelled entities, such as porphyrin labelled particles, can be exposed to a stabilized mixture of a luminescent probe and an oxidizer, which mixture only produces luminescence upon destabilization by the label based on the compound having formula I, the luminescence signal being determined. The signals obtained can be compared with the emission of light emitted by a stabilized mixture of luminescent probe and oxidizer containing a known number of particles, because there is a direct relationship between the number of labelled entities and the amount of radiation generated.

Chemiluminescence is used in a large number of analytical assays, including immunoassays and DNA probe analysis.

Generally, chemiluminescent assays are classified in two categories.

The first category comprises chemiluminescent assays wherein the quantifiable phenomenon consists of a very brief signal of only a few seconds. This signal is obtained after instantaneous injection of a triggering reagent into a reaction medium. Examples of this category are described by Schroeder et al. in Methods Enzymology 57 (1978) 424–445, who teach the use of coupling derivatives of luminol as a tracer; and by Weeks et al. in Analytical Applications of Bioluminescence and Chemiluminescence, Academic Press, 185–188 (1984), who teach the use of acridinium esters as a tracer. This first category of chemiluminescent assays has a number of known disadvantages of which the following two are explicitly mentioned. Firstly, the brevity of the signal leads to inconveniences in the measurements. Secondly, complicated measuring devices are needed, which require means for injecting reagents into the measuring chamber.

The second category comprises chemiluminescent assays wherein the quantifiable phenomenon consists of a longer-lasting signal, which can be measured for a significant time period. This category enables measurements to be repeated where appropriate and the samples to be prepared outside the luminometer.

The preferred embodiment of the present invention relates to compositions of the second category.

In Anal. Biochem. 145 (1985), 97–100 and in Clin. Chem. 31 (1985), 1335–1341, Thorpe et al. describe a procedure wherein a relatively stable and intense chemiluminescence signal is obtained. The peroxidaxe-dependent oxidation reaction of cyclic diacylhydrazides is enhanced by compounds such as synthetic luciferin, 6-hydroxybenzothiazole derivatives or substituted phenols. The term and constancy of the signal is only relatively long. The measurements must be performed within about 30–40 minutes.

In U.S. Pat. No. 5,108,893, it is disclosed that certain oxidase enzymes such as xanthine oxidase, choline oxidase, sarcosine oxidase and fumarate oxidase provide long-lived chemiluminescent detectable products upon reaction with chemiluminescent reagents, such as lucigenin, luminol and its derivatives. Said oxidase enzymes produce active oxygen-containing entities, such as superoxide anions, hydroxyl radicals and hydrogen peroxide. These chemiluminescent products known from U.S. Pat. No. 5,108,893 provide a signal which is stable with time and measurable during periods of at least several hours. Because of these advantages, said oxidase systems are particularly useful as a tracer for the detection of analytes in immunoassays, immunoblotting or nucleotide probe analysis as they provide long-lived light emitting entities which are stable for more than 20 hours with most emitting light for 120 hours or more. The oxidase systems can also be employed in immunoassay procedures using the avidin-biotin system. More in particular, in the specification of said patent, potentiation of the xanthine oxidase dependent oxidation of luminol by the iron/EDTA complex is clearly illustrated. In the examples a 10-fold increase in light output in the presence of the iron/EDTA complex is shown. No other procedures, evidence or other parameters are described which result in a (further) enhancement of the light output or triggering of the chemiluminescence by other means except oxidases.

The compounds of formula (I) used in accordance with the present invention provide an alternative chemiluminescence system providing long-lived chemiluminescent detectable products, and provide an improved chemiluminescence system.

In fact, the present invention relates in a further embodiment to a luminol-type chemiluminescent composition which comprises a porphyrin of formula I and an active oxygen providing source.

Preferred structures of protoporphyrins and porphyrins capable of being used in the process and in the composition of the present invention are deducted from ferroprotoporphyrin IX. This porphyrin-like structure, depicted in formula II, is the prosthetic group of hemoglobin, myoglobin, erythrocryorin, catalase, peroxidase and cytochromes of class B.

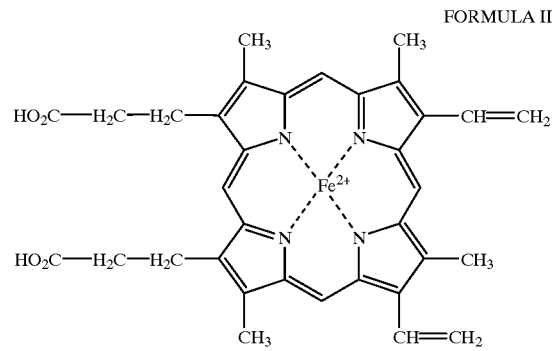

FORMULA II

In particular, ferriprotoporphyrins, e.g. chlorohemin (Formula III) or hematin (Formula IV), are examples of compounds which very efficiently adhere to entities such as molecules, beads, particles, microorganisms, cells and micels, and which very efficiently trigger the chemiluminescence as described.

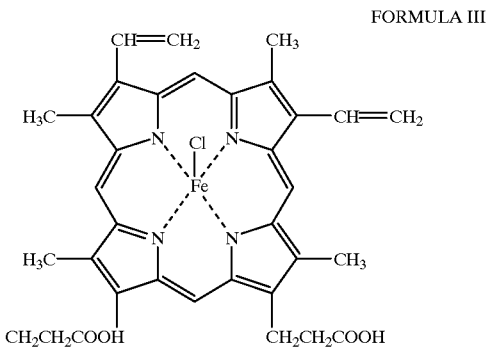

FORMULA III

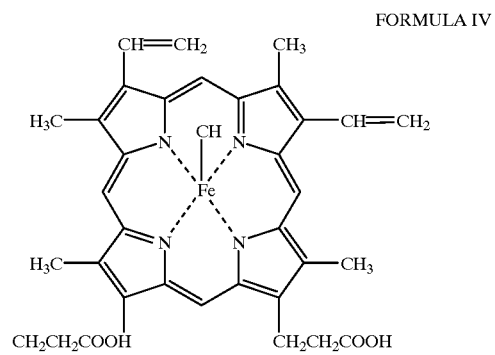

FORMULA IV

It is very surprising that oxidation of ferro-porphyrin-like structures to ferri-porphyrin-like structures leads to structures which actually triggers the chemiluminescence in accordance with the presently claimed invention. Such Fe(III) comprising structures are functionally dead enzymes being still capable of initiating chemiluminescence based on its protoporphyrin content. For instance, a heat-inactivated peroxidase will trigger the chemiluminescence in accordance with the present invention, but will not produce any chemiluminescence in the system described by Thorpe et al. described herein above.

In a luminol-type chemiluminescent composition, luminol or derivatives of luminol, such as isoluminol, are used as a chemiluminescent reagent. Suitable luminol derivatives are described in the above-mentioned articles of Schroeder et al. and Weeks et al. Preferably, luminol and/or isoluminol are used as the chemiluminescent reagent in the compositions of the invention.

In the chemiluminescent compositions of the described preferred embodiment of the present invention, an active oxygen providing source is required. In principle, any active oxygen providing source may be used. Suitable sources are peroxidase systems comprising a peroxidase as well as a substrate for this enzyme, peracids, and peroxides. In a preferred embodiment, the active oxygen providing source is perborate.

A chemiluminescent composition which comprises a porphyrin or protoporphyrin together with a perborate is found to be an alternative for the known oxidase enzyme system based compositions described in, e.g., U.S. Pat. No. 5,108,893. In addition, it has been found that by applying a chemiluminescent composition in which the oxidase is replaced by a porphyrin stability and storage problems are overcome. At a temperature of about 4° C., the storage of dry porphyrins useful in the present invention is almost indefinite. On the contrary, the oxidases used in the prior art have to be stored as solutions. A number of these oxidases, e.g. xanthine oxidase, are stable upon storage at 4° C. for only 6 months, whereas other oxidase solutions require storage at a considerably lower temperature of about −20° C. or even −80° C.

It is also possible to incorporate the compounds having formula I into a composition comprising an oxidase, such as xanthine oxidase, fumarate oxidase, choline oxidase, and/or sarcosine oxidase, as part of the active oxygen providing system. It has surprisingly been found that the presence of the compounds depicted by formula I in such systems give rise to an increase in light output of the chemiluminescence. More in particular, it is submitted that the present invention also relates to a porphyrin-mediated increase in light output of iron-EDTA catalyzed luminol-dependent chemiluminescence which is observed with several oxidases for the detection and quantification of analytes with immunoassays, DNA-probe analysis and to diagnostic kits designed to facilitate these assays.

Therefore, a preferred chemiluminescent composition of the invention comprises an oxidase enzyme system as the active oxygen providing source.

The compound of formula I can in accordance the present invention be used in the quantitative and/or qualitative analysis of various chemical and biochemical compounds. Furthermore, this composition allows the quantification of immunoassays, or hybridization reactions, particularly in small sample volumes.

In a further aspect, the present invention relates to adhesion or binding assays comprising the steps of
(i) providing a suspension, preferably an aqueous suspension, of entities to be tested;
(ii) mixing an effective detection amount of at least one compound defined by formula I with the suspension to form complexes with the entities to be tested;
(iii) removing excess compound of formula, preferably by centrifugation, magnetic separation or filtration;
(iv) incubating the complexed entities with a target surface to adhere the complexed entities;
(v) removing non-adhering material; and
(vi) detecting the adhered complexes.

Step (vi) can be carried out by e.g. chemiluminometric detection, comprising addition of a stabilized mixture of luminscent probe and oxidizer; and detection of the chemiluminescent signal, which signal is proportional to the number of labelled complexes.

Step (vi) can also suitably be carried out be radiometric detection and by fluorimetric detection.

The present invention further provides a method for the analysis of the diameter or particle size of particles or beads, comprising the steps of:
(i) providing a suspension of a determined number of particles or beads to be tested;
(ii) mixing an effective detection amount of a compound of formula I with said suspension;
(iii) removing excess label, preferably by centrifugation, magnetic separation or filtration;
(iv) radiometrically, fluorimetrically or chemiluminometrically registering of a signal, the signal being produced by an accurately known number of beads or particles;
(v) calculating the signal per particle or bead, which signal is proportional to its diameter or surface size.

In yet another embodiment, the invention relates to an uptake study which can be an in vitro or an in vivo method. This method comprises the steps of providing a suspension of entities to be tested; mixing an effective detection amount of at least one compound having formula I; removing excess label, preferably by centrifugation, magnetic separation or filtration; resuspending the labelled entities in an appropriate medium to be injected in a biological object; and tracing the injected labelled entities.

Further, the present invention relates to assay kits for quantifying entities, such as particles, beads, microorganisms, cells and so on, comprising as a chemiluminometric detection kit;
a first container containing a compound of formula I, preferably a ferriprotoporphyrin, as a label and a second container containing a stabilized mixture of luminescent probe and oxidizer;
as a radiometric detection kit:
a first container containing an istopically labelled compound of formula I and a second container containing either a scintillation cocktail or a scintillation proximity assay beads; or
as a fluorimetric detection kit;
a container containing a compound of formula I as a label.

BRIEF DESCRIPTION OF THE DRAWINGS

In the drawings which accompany this description:

FIG. 7 shows the increase in chemiluminescence of supernatant of a hematin-labelled and transfected virus-producing adherent cell line versus the chemiluminescence observed with the hematin-labelled non-virus producing adherent wild-type line.

DETAILED DESCRIPTION OF THE INVENTION

Figure 1:
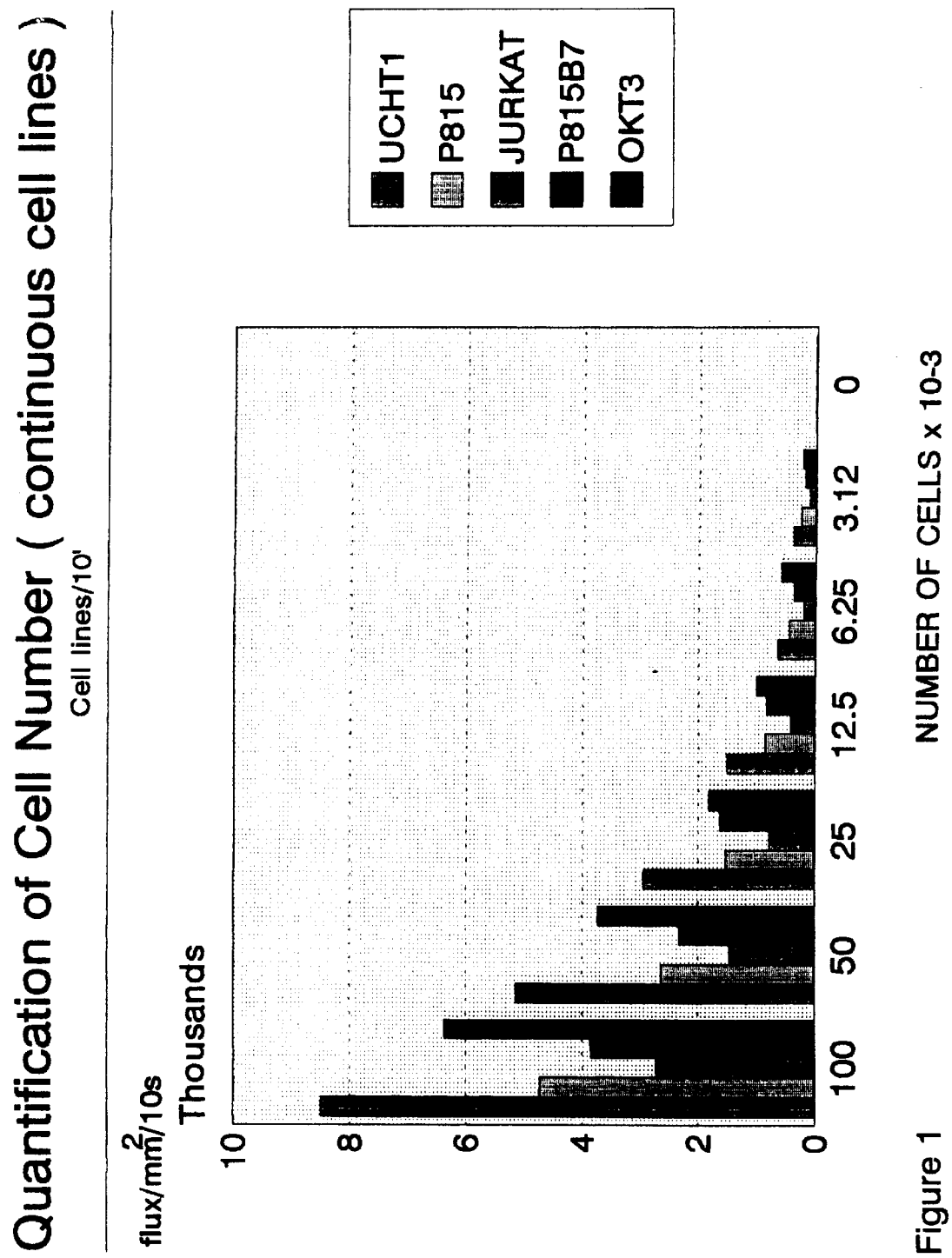
FIG. 1 shows the chemiluminescence signal (flux/mm$^2$/10 s) as a function of cell number (0–10$^5$) of different types of continuous cell lines, which are hematin-labelled and suspended in 100 μl of the stabilized luminol-oxidizer mixture.

In one aspect, the invention provides a process of quantifying the number of adherent or bound particles, beads, microorganisms or cells to target surfaces. In accordance with this process, an effective detection amount of e.g. ferriprotoporphyrin is ixed with aqueous suspensions of particles, beads, microorganisms or cells of interest. After removal of excess label, e.g. by centrifugation, magnetic separation or filter collection, labelled particles, -beads, -microorganisms or -cells are suspended at required densities in aqueous solutions of choice, Labelled particles, -beads, -microorganisms or -cells are then added to target surfaces, maintained under required reaction conditions for a period of time sufficient to bind or to adhere. Subsequently, non-bound or non-adherent labelled particles, -beads, -microorganisms or -cells are removed. Adherent or bound labelled particles, -beads, -microorganisms or -cells are detected:

1. Chemiluminometrically

Adding a sufficient amount of stabilized mixture of luminescent probe and oxidizer.

Chemiluminescence precursors for use in the present invention include 2,3-dihydro-1,4-phthalazinediones of the general formula V:

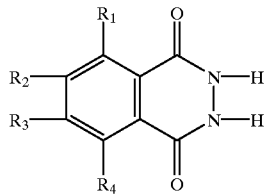

wherein $R_1$ is amino, and each of $R_3$ and $R_4$ is —M or an inert substituent. A particularly preferred chemiluminescence precursor is 5-amino-2,3-dihydro-1,4-phthalazinedione (luminol).

In one embodiment for carrying out the present invention, porphyrin labelled adherent or bound molecules, -particles, -beads, -microorganisms or -cells on a solid surface (i.e., membranes, dipsticks) enclosed in a transparent container or on microplates with transparent well bottom are placed on a high speed photographic film, such as a Polaroid film, cartridge. Immobilized labelled molecules, particles, -beads, -microorganisms or -cells are detected by injection of stabilized mixture of luminescent probe and oxidizer into the vessel to contact adherent or bound molecules, particles, beads, microorganisms or cells. Light emitted by virtue of a reaction between mixture of luminescent probe, oxidizer and porphyrin labelled molecules, -particles, -beads, -microorganisms or -cells are detected on the film. Alternatively, emitted light can be detected by other means such as by a photomultiplier tube or CCD (charge coupled device) cameras.

2. Radiometric

This method comprises the addition of a sufficient amount of an appropriate scintillation cocktail to molecules, particles, beads, microorganisms or cells labelled with an isotope (e.g. a beta emitter marked) compound of formula I and detection of the radiation emission by PMT or CCD cameras or direct detection of radiation by PMT of molecules, particles, beads, microorganisms or cells labelled with an isotope marked porphyrin and adhering or bound to surfaces coated with an appropriate solid scintillator.

3. Fluorimetric

In this detection technique adherent labelled particles, -beads, -microorganisms or -cells are exposed to a beam of light which the wavelength matches the excitation wavelength of the label based on a compound of formula I after or during which excitation the emission of light by the excited porphyrin is detected by a CCD camera or by photomultiplier tubes.

In addition, it is possible in accordance with the present invention to quantify an enzymatic activity such as of xanthine oxidase with a higher efficiency while using the porphyrin and oxidase system containing embodiment of the invention than is obtained while using the method of U.S. Pat. No. 5,108,893.

Further, it is noted that the luminol-dependent chemiluminescence is highly pH-dependent. With e.g. the xanthine oxidase being present in the chemiluminescence mixture of the invention, the pH optimum is 10.3. The same effects can be observed with compositions of which the chemiluminescence is triggered by a porphyrin. With varying pH-values, a varying light output is observed. These variations in light output may be used to detect and determine pH variations in solutions of interest.

In a further aspect, the invention relates to a process for increasing the light output of a luminol-type chemiluminescence composition comprising an oxidase enzyme system as an active oxygen providing source, wherein a light-output increasing amount of a porphyrin of the formula I is used. It has been found that the addition of minute amounts of porphyrins and/or protoporphyrins to the compositions of the signal reagent described in U.S. Pat. No. 5,108,893, leads to a 10–100 fold increase in light output of the oxidase enzyme system. This fact will be demonstrated hereinbelow with respect to the xanthine oxidase/hypoxanthine/luminol/Fe-EDTA mixture. Furthermore, the use of protoporphyrins enables the threshold of detection of the oxidase enzyme system to be lowered by at least a factor 10.

The advantageous effect of this preferred embodiment already occurs while using a very low amount of less than 25 μM of the porphyrin-like compound. Preferably an amount of between 10 and 100 μM of a compound of formula I is present in a composition to be used for this purpose.

Preferably, hemin and/or hematin are added together with perborate as the active oxygen providing source to signal reagent compositions. The addition of hematin and/or hemin does not alter the overall stability of the signal which is produced in their absence.

Furthermore, the invention relates to a process for providing long-lived chemiluminescent detectable products, wherein a porphyrin of the formula I is used in combination with an active oxygen providing source.

In preferred embodiments, the active oxygen providing source is perborate. Other suitable oxidants than perborate which react with compounds of formula I to cause excitation of a chemiluminescence precursor so that it emits light in a chemiluminescence reaction are peroxides, e.g. hydrogen peroxide, endoperoxides, and peracids, as well as oxidizer producing enzymes.

More in particular, instead of oxidase systems, (proto) porphyrins of the formula I can be used as triggers of the chemiluminescence of luminol-type perborate solutions. Further, these solutions normally comprise an enhancer, e.g. a transition metal complex, preferably an iron-complex, such as a Fe-EDTA complex. However, the presence of a transition metal complex as an enhancer is not necessary or essential. Chelators such as deferrioxamine or ethylene diamine tetraacetic acid are added as stabilizer for mixtures of luminescence precursor and oxidizer.

The composition of the invention normally incorporates a buffer. Preferably, a borate buffer is used, because of its buffering capacity around pH 10.3. However, other buffers showing a comparable buffer capacity in the pH range of about 9.5–12, and preferably of about 10–11, may be used, as well. Suitable buffering substances are phosphate buffers, tris(hydroxymethyl)aminomethane, carbonate buffers and borate buffers.

It is found that the light output observed is dependent on the presence of perborate and can be made dependent on the concentration of the porphyrin.

The introduction of porphyrins leading to an increase in light output of luminol-dependent oxidase luminescence in the presence of perborate can be employed in immunoassay procedures, chemiluminescent detection of oxidase labeled nucleotide probes or in general any chemiluminescent oxidase system designed to detect an analyte wherein a specific binding pair ligand is coupled with an enzymatic or substrate tracer.

In test procedures it came out that by raising the concentration of the perborate from 20 $\mu$M to at least 100 $\mu$M in the signal reagent composition, more in particular in a composition comprising 200 mM borate, 1 mM hypoxanthine, 25 $\mu$M luminol, 100 $\mu$M sodium perborate, and 62.5 $\mu$M of an EDTA-Fe complex, pH 10.3, the signal reagent can be used for the detection of porphyrins, including porphyrin labeled analytes, antibodies or porphyrin containing proteins, such as hemoglobin, cytochromes, non-functional peroxidases, and catalase. Furthermore, as the chemiluminescence using porphyrins occurs in the absence of xanthine oxidase, the hypoxanthine substrate can be omitted.

The present invention also relates to kits for the quantification of porphyrins. A kit of the invention comprises 0.2 M borate buffer, pH 10.3 containing minimal 100 $\mu$M perborate, 25 $\mu$M luminol, 62.5 $\mu$M Fe-EDTA, and a positive control sample containing a porphyrin of formula I. Another suitable reagent composition contains 0.1 M borate buffer (pH 9.50) containing 6.5 mM perborate, 3.4 mM EDTA and 0.1 mM luminol.

Finally, the present invention relates to kits for the enhancement of the light output obtained with oxidase enzyme systems, such as those described in U.S. Pat. No. 5,108,893. Such a kit of the invention comprises 0.2 M borate buffer, pH 10.3 containing less than 25 $\mu$M perborate, and optionally no perborate at all, 25 $\mu$M luminol, 62.5 $\mu$M Fe-EDTA, and a positive control sample containing the enzyme of the afore mentioned oxidase enzyme system.

The kit for determining the presence of a predetermined target nucleotide sequence in the DNA of a biological sample may be assembled in the following way. First, target nucleotide sequences are applied to a nitrocellulose membrane, a solid support or any applicable support which may be produced in the form of strips. The support is, after drying and baking, subjected to hybridisation with a highly specific DNA-probe. This DNA-probe is prelabeled with a substance capable of binding with high affinity to a second substance of which the presence is required for the production of the chemiluminescence in the final step. Preferably, digtoxigenin or biotin are used as a label of the DNA-probe. The prelabeled probe is detected with xanthine oxidase labeled with anti-digoxigenin or streptavidin. Finally, the xanthine oxidase is detected by means of chemiluminescence as outlined in the examples hereinbelow.

The described kits may be used for the detection and quantification of any antigen present in biological samples. The antibody of interest is applied to a solid support, preferably a membrane of microwells. To this fixed antibody preparation, the biological sample of interest is added and incubated for a predetermined period of time at a predetermined temperature. In a second step, monoclonal or polyclonal secondary antibody bound to xanthine oxidase is added. After removal of excess secondary antibody-xanthine oxidase conjugate, the xanthine oxidase is detected first by adding hematin-solution in water prior to the addition of signal reagent.

In one of the preferred embodiments, the invention uses protoporphyrins to enhance the light output of luminol-dependent chemiluminescent reactions which are based on the simultaneous production of hydrogen peroxide and superoxide. More in particular, the enhancement of the light output is observed with enzymes such as xanthine oxidase, producing superoxide and hydrogen peroxide, and with superoxide generating systems to the presence of perborate.

According to a preferred process of the invention, excess porphyrin is coupled to an antigen or antibody to be determined and the chemiluminescent composition of the invention used for the assay contains increased concentrations of perborate. Porphyrins coupled to antigens or antibodies may provide so-called "direct" labelling systems. Until the finding underlying the present invention, all other chemiluminescent detection systems are based on the labelling of an antigen or antibody with an enzyme. In these known systems, only one enzyme can usually be bound to a specific antibody, because of the relatively high molecular weight of the enzyme in relation to the antibody; the molecular weight of xanthine oxidase is for example about 150,000 u. On the contrary, porphyrin-like structures have a relatively low molecular weight in the order of 600 u. This makes that porphyrin-labelling of molecules of interest can be done in excess or at saturation. Several hundreds of porphyrins can be bound to an antibody instead of only one. The advantages of this multiple binding possibility will be clear to a person skilled in the field of the present invention.

According to another preferred embodiment, excess porphyrin can be coupled or be bound to xanthine oxidase. In this embodiment, the porphyrins directly provide the enhancement of the light output of the luminescence.

Furthermore, the porphyrins to be used in accordance with the present invention may be encapsulated in liposomes using well known techniques. The advantage of encapsulated porphyrins resides in the fact that thousands of molecules, e.g. hematins or hemins, may be contained in one liposome. This liposome can be destabilized by a specific molecule, which one would like to detect. Destabilization can e.g. be effected by reactive oxygen species (superoxide, singlet oxygen, hydroxyl radicals) or by a change in pH, or by the addition of surface active compounds, such as detergents. By the destabilization, thousands of porphyrin molecules are set free, which molecules are capable of triggering the chemiluminescence reaction.

In accordance with a process of the present invention, an effective detection amount of porphyrin is that amount of porphyrin needed to provide detectable luminescent signal in proportion to the number of particles, beads, microorganisms or cells to be counted. An effective detection amount varies inter alia with the number of particles, beads, microorganisms or cells and the nature of the porphyrin.

Where the number of particles, beads, microorganisms or cells is from 0 to about $10^9$/milliliter (ml) and the luminescent probe is luminol, the effective detection amount of porphyrin, used for labelling, is from about $10^{-3}$ M to about $10^{-5}$ M.

Labelling and detection conditions include: temperature, pH value, osmolality, tonicity and the like. Typically, the temperature can range from about 5° C. to about 50° C. and, preferably, from about 20° C. to about 40° C. The pH can range for labelling from about 6 to about 8.5 and, preferably from 6.5 to 7.5. Detection pH can range from 7.5 up to 12.5 and preferably from a value of about 8 to a value of about 10.5.

The maintenance time of porphyrin labelling is generally from 5 up to 20 minutes, preferably 10 minutes.

As used herein, a particle means any particulate phase with undefined shape, including molecules, micelles and coloids and size ranging from submicroscopic to about 1 cm. A bead means either a solid sphere or hollow sphere, including liposomes and size ranging from submicroscopic to about 1 cm.

In yet another aspect, the present invention contemplates an assay kit for detecting and quantifying particles, beads microorganisms or cells comprising:

A first container containing porphyrin label as such (chemiluminometric and fluorimetric detection) or radioactive labelled. The porphyrin label can be suspended or dissolved in a suitable medium or can be in a dry form. The only limitation on the formulation is that a particular formulation should ensure stability to the label such that the label does not undergo chemical alteration during storage.

The assay kit can further comprise a second container that contains:

A stabilized mixture of luminescence precursor and oxidizer, in an amount sufficient to perform at least one quantification assay, wherein the stabilized mixture interacts with particles, beads, microorganisms or cells labelled with the porphyrin label of the first container in an amount proportional to their number. A stabilized mixture of luminescence precursor and oxidizer can also exist as a suspension, solution or in dy form (e.g. tablets).

A suitable scintillatin cocktail for the detection of porphyrin isotopically labelled with a beta-emitter, in an amount sufficient to perform at least one quantification assay.

By way of example, an exemplary kit comprises a first container containing, 1.1 ml of 1.5 mM hematin (porphyrin label) in dimethylsulfoxide (DMSO) and a second container containing 110 ml of 6.5 mM sodiumperborate (oxidizer) in 0.1 M borate buffer pH 9.5 containing 3.5 mM EDTA (stabilizer) and 0.1 mM luminol (luminescence precursor).

If stored properly at about 4° C., those solutions remain stable for several months.

In a preferred embodiment, the first and second container are labelled with indicia setting forth the nature, amount or concentration and effective amounts of the ingredients contained herein.

The invention will be described in further detail while referring to the following examples and to the drawings, wherein

EXAMPLE 1

Quantification of Cell Number (Continuous Coil Lines)

A. Materials and Methods

UCHT1, P815, Jurkat T-cells, P81587 and OKT3 cells were collected, centrifuged and resuspended in Dulbecco's PBS at a density of $1.10^6$ cells/ml in a standard 15 ml Falcon tube. Next, to 1 ml of each cell suspension, 10 µl of a hematin stock solution (1 mg/ml in DMSO) was added and left after gentle mixing at room temperature for about 10 minutes. After another gentle mix, cells were left for another 5 minutes at room temperature, after which 4 ml of PBS were added and cells gently aspirated. After centrifugation at 150 g, 10 minutes, cell pellets were resuspended in another 4 ml of PBS and washed again to make sure all excess hematin label was removed.

Finally, cell pellets were resuspended at a density of $10^6$/ml. Next, cells were plated into individual wells of a white microtiter plate so that the number of cells ranged from 0 cells/well to about 100,000 cells/well in a total volume of 100 µl PBS/well.

B. Detection of the Chemiluminescence

Next to each well, 100 µl of a stabilized luminol/perborate composition (0.1 M borate buffer pH 9.5 containing 6.5 mM perborate, 3.4 mM EDTA and 0.1 mM luminol) were added and the chemiluminescence produced after 10 minutes was recorded at ambient temperature using a CCD camera.

Results are shown in FIG. 1.

EXAMPLE 2

Quantification of Cell Number (Isolated Cells)

Macrophages, isolated by bronchial lavage of mice, were pooled and concentrated after washing in Dulbecco's PBS at a density of $10^6$ ml. Next, to 1-ml macrophage suspension, 10 µl of hematin (1 mg/ml in DMSO) were added and cells incubated and washed as set forth above in Example 1.

Emitted chemiluminescence was detected, 10 minutes after exposure of cells to 100 µl of stabilized luminol oxidizer composition as set forth above in Example 1.

Figure 2:
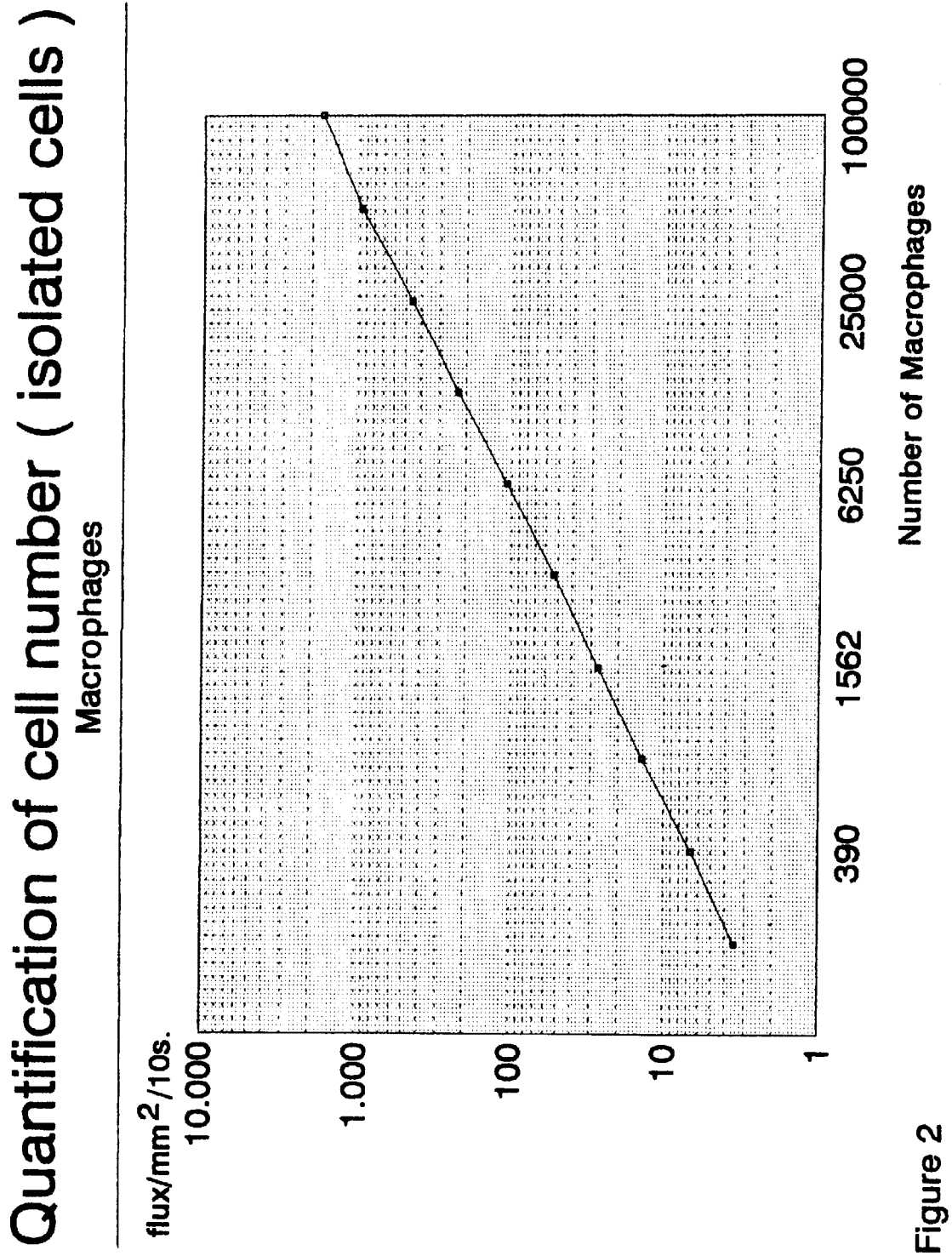
FIG. 2 shows the chemiluminescence signal (flux/mm$^2$/10 s) as a function of cell number (0–10$^5$) of hematin labelled mouse macrophages.

Results are shown in FIG. 2.

The data in FIG. 1 and 2 show that the chemiluminescence observed with hematin-labelled cells is proportional to cell number. These data further show that labelling of continues cell lines as well as labelling of isolated cells are feasible.

EXAMPLE 3

Quantification of Inert Particles

As an example of inert particles, uncoated Dynabeads M-450, commercially available as a suspension of $2.10^8$ beads/ml from Dynal A.S., N-0210 Oslo, Norway, were washed and suspended at a density of $10^7$ beads/ml in Dulbecco's PBS. Next, 10 μl of a hematin stock solution (1 mg/ml in DMSO) were added and beads incubated at room temperature for 10 minutes while gently mixed on a roto-rack. After 10 minutes of incubation, beads were separated from the incubation mixture by magnetic separation, washed twice with PBS and finally resuspended at a density of $10^7$ beads/ml.

Finally, the labelled beads were plated into individual wells of a white 96 well microtiter plate so that the number of beads ranged from 0 beads/well to about $10^6$ beads/well in a total volume of 100 μl PBS/well. Next the chemiluminescence was detected by the addition of 100 μl stabilized luminol-oxidizer as set forth above.

Figure 3:
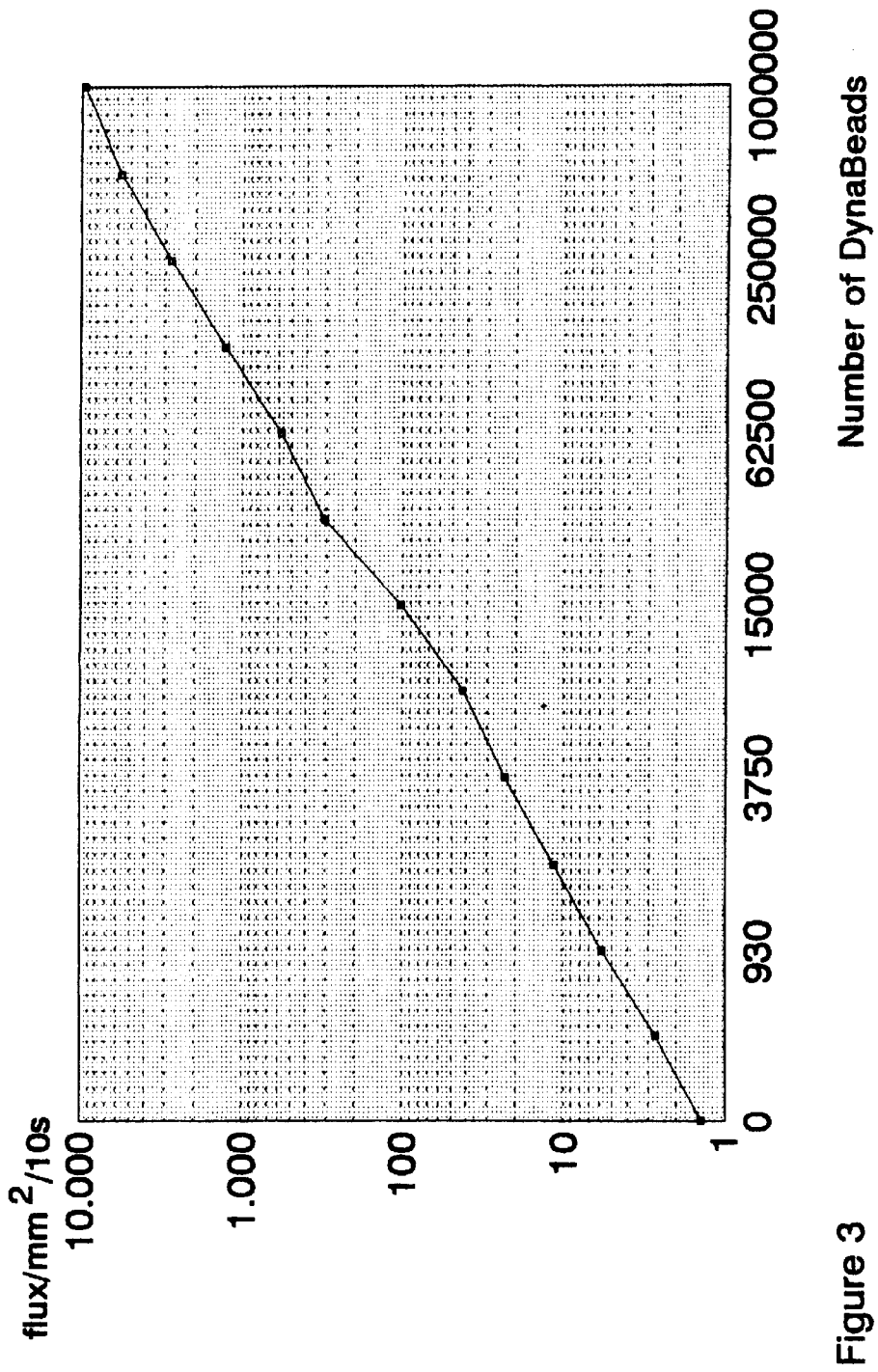
FIG. 3 shows the chemiluminescence signal (flux/mm$^2$/10 s) as a function of the number (0–10$^6$) hematin-labelled Dynabeads M-450 suspended in 100 μm PBS, 10 minutes after the addition of 100 μl of the stabilized luminol-oxidizer mixture.

Results of this experiment are summarized in FIG. 3.

EXAMPLE 4

Quantification of Microorganisms

As an example, a suspension of $10^8$ Staphylococci aureus was prepared in Dulbecco's PBS starting from a crude suspension of Staph. aureus grown overnight in Trypcaso Soya Broth.

After washing, 1 ml of Staph. aureus suspension was labelled by the addition of 10 μ. hematin stock solution (1 mg/ml in DMSO) as set forth above in the example of the Dynabeads.

After 10 minutes of labelling at ambient temperature, the Staph. aureus suspension was centrifuges (450 g/5 min) and the bacterial pellet washed with 5 ml PBS. This washing procedure was repeated twice after which the pellet of labelled bacteria was resuspended at a density of $10^8$ bacteria/ml.

Next a serial dilution of bacteria was prepared in wells of a white microtiter plate from 0 up to $10^7$ bacteria in a total volume of 100 μl Dulbecco's PBS. Chemiluminescence was initiated and detected as set forth above in the example of the Dynabeads.

Figure 4:
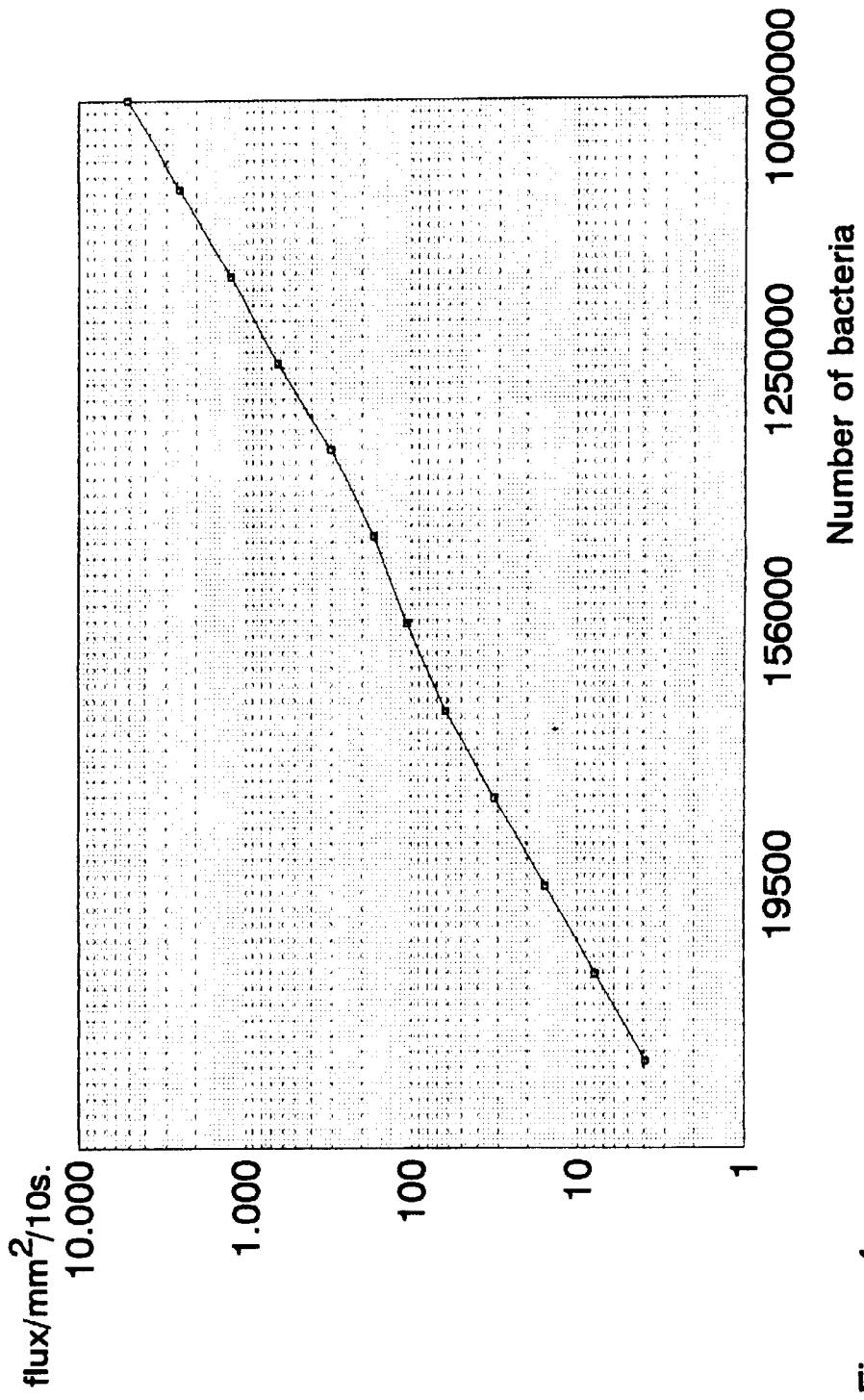
FIG. 4 shows the chemiluminescence signal (flux/mm$^2$/10 s) as a function of the number of hematin labelled *Staphylococcus aureus* (0–10$^7$).

Results are summarized in FIG. 4.

EXAMPLE 5

Quantification of the Number of Adherent Bacteria of Different Strains to Nasal Cell Monolayers Suspensions of two different strains of Staph. aureus (A,B) were prepared at a density of $10^9$/ml in PBS and labelled with hematin as set forth above in Example 4. $10^8$, $5.10^7$, $2.5.10^7$ and 0 bacteria in a total volume of 100 μl were incubated with confluently grown adherent human nasal epithelial cell monolayers. After 1.5 hours incubation at 37° C. in a humidified incubator (air, 5%, $CO_2$) non-adherent bacteria were removed by gentle washing. Next, 100 μl Dulbecco's PBS were added to wells to be measured. Chemiluminescence was initiated and measured as described in Example 4.

Figure 5:
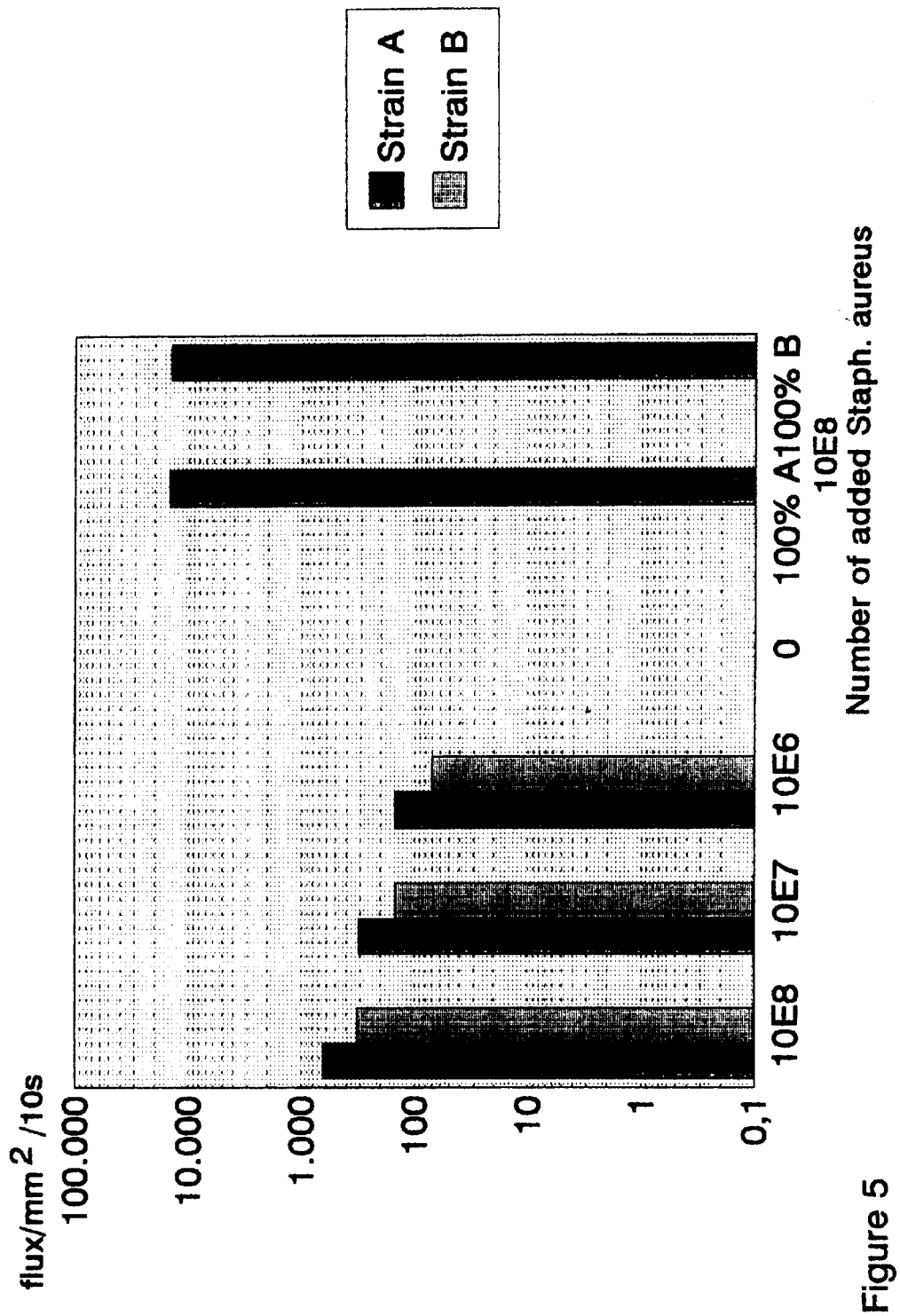
FIG. 5 shows the chemiluminescence signal produced by adhering *Staphylococcus aureus* to nasal epithelial cell monolayers.
Figure 6:
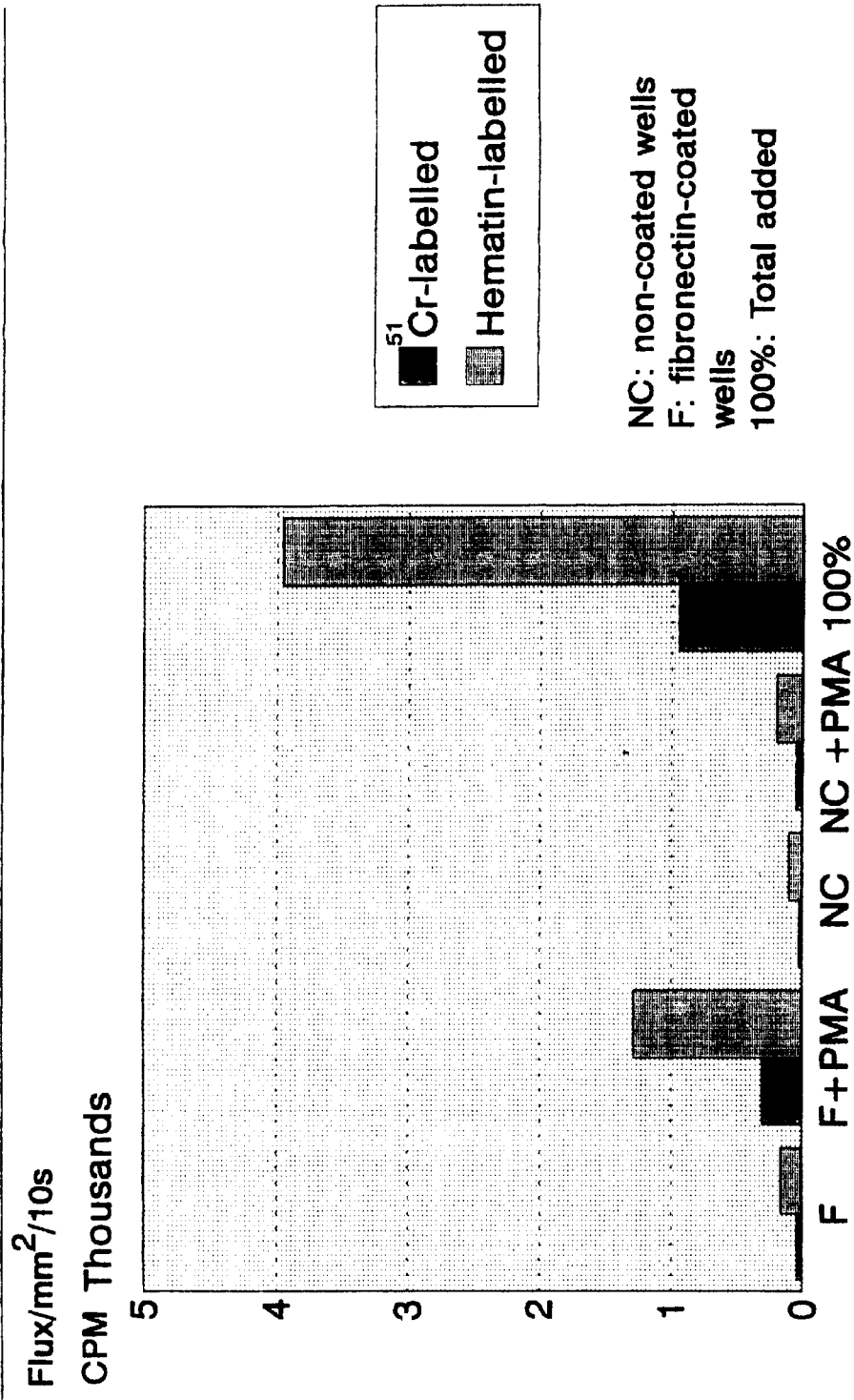
FIG. 6 shows the difference in chemiluminescence observed with non-stimulated- and PMA-stimulated hematin-labelled CD4-positive-T-cells on fibronectin-coated surfaces and non-coated surfaces of a tissue culture microtiter plate.

Results are summarized in FIG. 5 and show, differential adhesion of the different Staph. aureus strains.

EXAMPLE 6

Adhesion of PMA stimulated CD4+-T Cells on Fibronectin Coated Microtiter Wells CD4+ T cells were isolated from a T-cell preparation according to standard procedures starting from a human whole blood sample which was first centrifuges over a Ficoll-Hypaque gradient. CD4+-T cells were isolated by magnetic separation using Dynabeads.

Finally, CD4+-T cells were suspended at a final concentration of $10^6$/ml in PBS.

10 μl hematin (1 mg/ml in DMSO) were added to label the T-cells as set forth above in Example 2.

After labelling and washing, CD4+-T cells were resuspended at a density of $10^6$/ml in 50% (VV) PBS/Hanks albumine (0.1%). In parallel, another aliquot of CD4+-T cells was $^{51}$Cr labelled according to standard protocols.

Next, to triplicate wells of a white microtiter plate, either fibronectin coated or non-fibronectin coated, first 50 μl PBS/HSA were added or 50 μl PBS/HSA containing $10^{-6}$ M phorbol myristate acetate (PMA).

Next, 50 μl hematin labelled T-cells or $^{51}$Cr-labelled T-cells were added to the different well compositions.

After 2 hours of incubation at 37° C. (humidified air, 5% $CO_2$), non adherent cells were gently removed. Next, $^{51}$Cr-labelled cells were lysed, using 100 μl of a Triton X-100 lysis solution and radioactivity determined by gamma-counting. After removing non-adherent hematin-labelled CD4+-T-cells 100 μl PBS were added to the wells and chemiluminescence was counted 10 minutes after the addition of 100 μl of the stabilized luminol-oxidizer solution.

Results are summarized in FIG. 7.

EXAMPLE 7

Hematin Labelling and Virus Producing Cell Lines

DSN non-virus producing and DSMOJD21MDR1 transfected and virus producing cell monolayers were grown confluently in petridishes (Falcon) and labelled with hematin 100 μg hematin contained in 10 ml Dulbecco's PBS for 10 minutes. After labelling, cells were washed 2 times with excess PBS (controls (no hematin label)) were treated accordingly, except the PBS did not contain hematin label.

Next, 10 ml IMDM (without fetal calf serum) was added to the dishes and incubation started overnight. The next day, 10 μl supernatant, taken from each dish, were transferred to wells of a white microtiter plate. 100 μl stabilized luminol-oxidizer solution were added and the chemiluminescence was recorded 10 minutes after. Results are shown in FIG. 7. No significant signal was produced with the supernatant of the controls (no label). However, a significant difference in chemiluminescence was observed with supernatant obtained from the labelled but non-virus producing line and supernatant from the labelled virus-producing monolayer.

Increas in chemiluminescence observed with supernatant derived from the latter suggests the present invention allows to detect processes of virus budding.

Finally, when monolayers of non-labelled and non-producing DSN cells were indubated with supernatant of the labelled pJD214 virus producing cell monolayer, an increase in chemiluminescence after the addition of luminol-oxidizer solution was observed with washed pjD214 cell monolyers after an initial lag phase.

Figure 8:
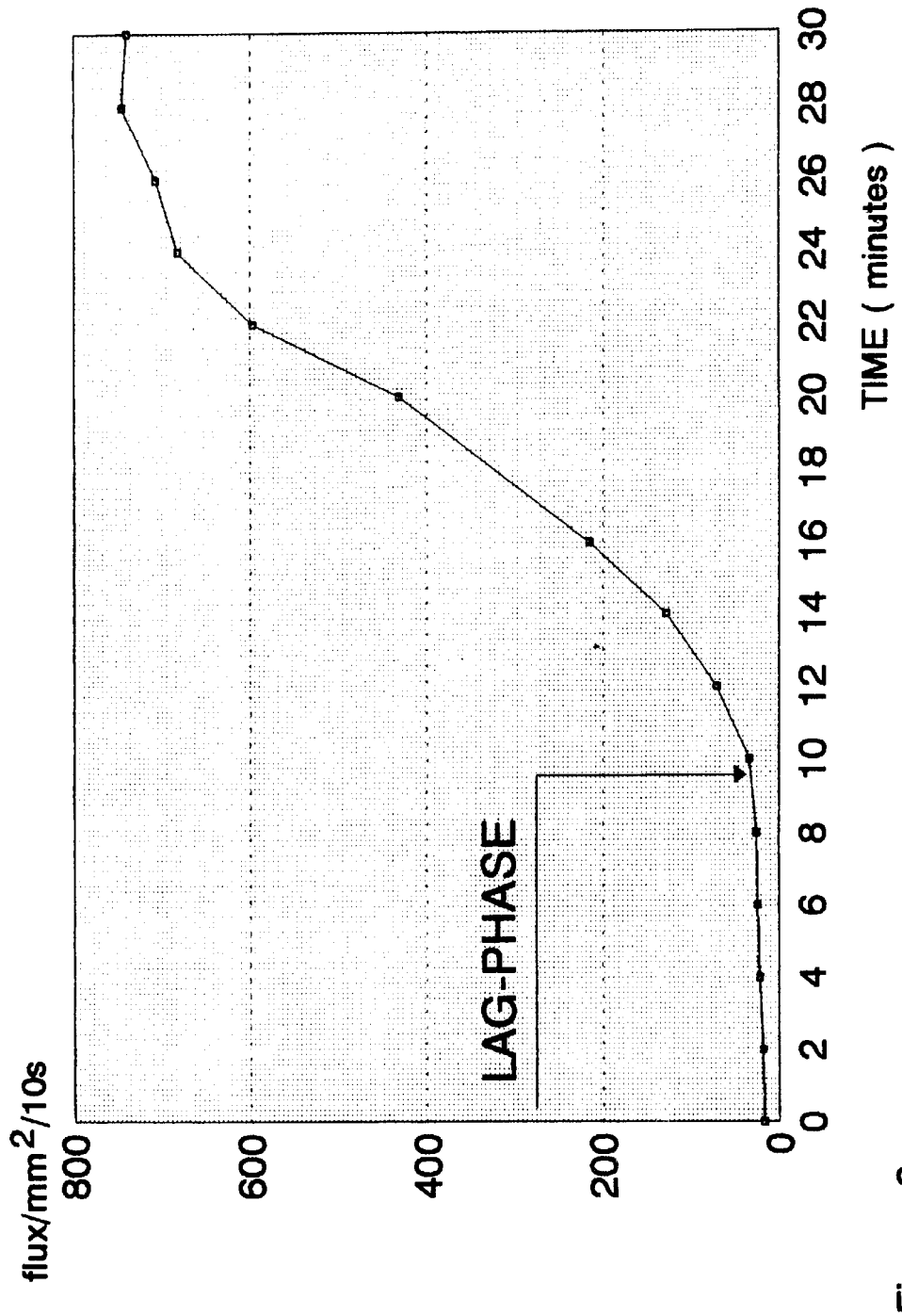
FIG. 8 shows chemiluminescence observed with cells infected by hematin-labelled viruses.

These results, shown in FIG. 8, are suggesting the stabilized luminol-oxidizer solution detects hematin-labelled virus within the DSN cells. The observed lag-phase suggest, luminol-oxidizer solution penetrates slowly in the cells where it gradually becomes destabilized by the hematin brought in by the virus.

I claim:

1. A process for quantifying entities having a hydrophobic part or a part capable of hydrophobic interaction, comprising the steps of (a) mixing an effective detection amount of a (proto-) porphyrin represented by formula (I)

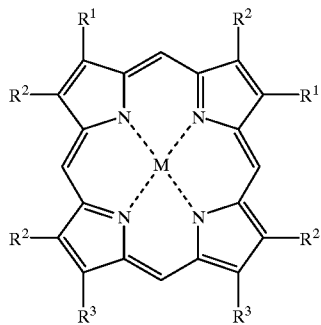

wherein
R$^1$ independently represents a radical selected from the group consisting of —CH(OH)—CH$_3$, —CH═CH$_2$, —CH$_2$—CH$_3$, —H, —COCH$_3$, —CHO, —CH(OH)—CH$_2$OH, and —CH═CHO$_2$H;
R$^2$ independently is selected from C$_{1-3}$ alkyl;
R$^3$ independently represents an aryl or aralkyl group; and
M is a metal selected from Fe, Co, Ga, Sn, Zn, ⁻Cr, Mg, Ni, Ge, and Cu,
with a sample suspected to contain entities to be detected;
(b) collecting the (proto)porphyrin containing complexes formed; and
(c) detecting and quantifying the collected complexes by chemiluminescence, radiometric detection, or fluorimetric detection.

2. The process of claim 1, wherein step (c) is carried out using chemiluminescence.

3. The process of claim 2, wherein an active oxygen providing source is used in the detection.

4. The method of claim 2 or 3, wherein an active oxygen providing source is perborate.

5. The method of claim 2 or 3, wherein the active oxygen providing source is an oxidase enzyme system.

6. The method of claim 2 or 3, wherein as a chemiluminescent reagent luminol or isoluminol is used.

7. Adhesion or binding assay comprising the steps of
(i) providing a suspension of entities to be tested;
(ii) mixing an effective detection amount of at least one compound having formula I as defined in claim 1, with the suspension to form complexes with the entities to be tested;
(iii) removing excess compound of formula I;
(iv) incubating the complexed entities with a target surface to adhere the complexed entities;
(v) removing non-adhering material; and
(vi) detecting the adhered complexes by chemiluminescence, radiometric detection, or fluorometric detection.

8. A process of claim 1 wherein R$^2$ is methyl.

9. A process of claim 1 wherein R$^3$ is phenyl.

10. An assay of claim 7 wherein excess compound of formula I is removed by centrifugation, magnetic separation, or filtration.

11. An assay of claim 7 wherein the suspension of (i) is an aqueous suspension.

* * * * *